(12) United States Patent
LaBelle et al.

(10) Patent No.: US 10,724,066 B2
(45) Date of Patent: Jul. 28, 2020

(54) SALIVA GLUCOSE MEASUREMENT DEVICES AND METHODS

(71) Applicant: ARIZONA BOARD OF REGENTS ON BEHALF OF ARIZONA STATE UNIVERSITY, Scottsdale, AZ (US)

(72) Inventors: Jeffrey LaBelle, Tempe, AZ (US); Chi Lin, Tempe, AZ (US); Jonus Reyna, Tempe, AZ (US); Amnah Alkhan, Tempe, AZ (US); Cael Muggeridge, Tempe, AZ (US); Susan Sheffield, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 155 days.

(21) Appl. No.: 16/068,877

(22) PCT Filed: Jan. 27, 2017

(86) PCT No.: PCT/US2017/015434
§ 371 (c)(1),
(2) Date: Jul. 9, 2018

(87) PCT Pub. No.: WO2017/132565
PCT Pub. Date: Aug. 3, 2017

(65) Prior Publication Data
US 2019/0024131 A1 Jan. 24, 2019

Related U.S. Application Data

(60) Provisional application No. 62/288,747, filed on Jan. 29, 2016.

(51) Int. Cl.
*G01N 27/327* (2006.01)
*C12Q 1/00* (2006.01)
(Continued)

(52) U.S. Cl.
CPC .......... *C12Q 1/006* (2013.01); *A61B 5/14532* (2013.01); *G01N 27/31* (2013.01);
(Continued)

(58) Field of Classification Search
CPC .......................................... G01N 27/327-3272
See application file for complete search history.

(56) References Cited

U.S. PATENT DOCUMENTS 8,815,178 B2 8/2014 Bishop
9,766,199 B2 9/2017 Dastoor et al.
(Continued)

FOREIGN PATENT DOCUMENTS

WO 2010111484 A1 9/2010
WO 2015183893 A1 12/2015
(Continued)

OTHER PUBLICATIONS

Bishop et al., "A Disposable Tear Glucose Biosensor—Pat 1: Design and Concept Testing" Journal of Diabetes Science and Technology vol. 4, issue 2, Mar. 2010 (Year: 2010).*
(Continued)

*Primary Examiner* — Alexander S Noguerola
(74) *Attorney, Agent, or Firm* — Quarles & Brady LLP; Jessica L. Lewis (57) ABSTRACT

Devices and methods capable of detecting glucose in saliva (FIG. 12). The devices feature a sensor having a substrate containing electrodes and one or more reagents on the electrodes. A detection device is operably coupled with the sensor to detect glucose based on measurement of an electrical parameter when electricity is applied to the electrode.

6 Claims, 12 Drawing Sheets

(51) Int. Cl.
*G01N 27/403* (2006.01)
*G01N 27/70* (2006.01)
*G01N 27/31* (2006.01)
*A61B 5/145* (2006.01)

(52) U.S. Cl.
CPC ..... *G01N 27/3272* (2013.01); *G01N 27/3273* (2013.01); *G01N 27/403* (2013.01); *G01N 27/70* (2013.01)

(56) References Cited

U.S. PATENT DOCUMENTS

| | | | |
|---|---|---|---|
| 10,386,321 | B2 | 8/2019 | LaBelle |
| 2001/0023324 | A1 | 9/2001 | Pronovost et al. |
| 2008/0177166 | A1* | 7/2008 | Pronovost ............. C12Q 1/006 600/365 |
| 2013/0026050 | A1 | 1/2013 | Harding et al. |
| 2013/0075276 | A1 | 3/2013 | Hoashi et al. |
| 2014/0262830 | A1* | 9/2014 | Cha ........................ C12Q 1/006 205/777.5 |
| 2015/0037827 | A1 | 2/2015 | Dastoor et al. |
| 2017/0202691 | A1 | 7/2017 | LaBelle |
| 2019/0046092 | A1 | 2/2019 | LaBelle |
| 2019/0150815 | A1 | 5/2019 | LaBelle |

FOREIGN PATENT DOCUMENTS

| | | |
|---|---|---|
| WO | 2018148236 A1 | 8/2018 |
| WO | 2018175448 A1 | 9/2018 |
| WO | 2019178588 A1 | 9/2019 |

OTHER PUBLICATIONS

Kumar et al., "Saliva: Can it be a Supportive Marker for Oxidative Stress among Rheumatoid Arthritis Patients?," Journal of Dental Applications, vol. 2, issue 5, 2015, pp. 0210-0213 (Year: 2015).*
Abikshyeet P, et al. Glucose estimation in the salivary secretion of diabetes mellitus patients. Diabetes Metab Syndr Obes 2012;5:149-54.
Alberti KGMM, et al. Definition, diagnosis and classification of diabetes mellitus and its complications. Part 1: diagnosis and classification of diabetes mellitus. Provisional report of a WHO consultation. Diabet Med 1998;15:539-53.
Amer S, et al. Salivary glucose concentrations in patients with diabetes mellitus—a minimally invasive technique for monitoring blood glucose levels. Pak J Pharm Sci 2001;14:33-7.
American Diabetes Association. Diagnosis and classification of diabetes mellitus. Diabetes Care 2010;33:S62-9.
American Diabetes Association. Economic costs of diabetes in the US in 2012. Diabetes Care 2013;36:1033-46.
Ben-Aryeh H, et al. Salivary composition in diabetic patients. J Diabet Complications 1988;2:96-9.
Bishop DK, et al. A disposable tear glucose biosensor—part 1: design and concept testing. J Diabetes Sci Technol 2010;4:299-306.
Carda C, et al. Structural and functional salivary disorders in type 2 diabetic patients. Med Oral Patol Oral Cirugia Bucal 2006;11:209.
Centers for Disease Control and Prevention. National diabetes statistics report: estimates of diabetes and its burden in the United States, 2014. Atlanta GA US Dep Health Hum Serv 2014.
Centers for Disease Control. Number of Americans with diabetes expected to double or triple by 2050. Retrieved Apr. 2010;20:2011.
Dawes C, et al. The effects of gum chewing, four oral hygiene procedures, and two saliva collection techniques, on the output of bacteria into human whole saliva. Arch Oral Biol 2001;46:625-32.
De Jong M, et al. The growth of oral bacteria on saliva. J Dent Res 1987;66:498-505.
Du Y, et al. An on-chip disposable salivary glucose sensor for diabetes control. J Diabetes Sci Technol 2016:1932296816642251.

Ferri S, et al. Review of glucose oxidases and glucose dehydrogenases: a bird's eye view of glucose sensing enzymes. J Diabetes Sci Technol 2011;5:1068-76.
Forbat L, et al. Glucose concentrations in parotid fluid and venous blood of patients attending a diabetic clinic. J R Soc Med 1981;74:725-8.
Gupta S, et al. Comparison of Salivary and Serum Glucose Levels in Diabetic Patients. J Diabetes Sci Technol 2015;9:91-6.
Hayes M, et al. The breakdown of glucose, xylitol and other sugar alcohols by human dental plaque bacteria. Arch Oral Biol 1978;23:445-51.
Heinemann L. Finger pricking and pain: a never ending story. J Diabetes Sci Technol 2008;2:919-21.
Holman RR, et al. 10-year follow-up of intensive glucose control in type 2 diabetes. N Engl J Med 2008;359:1577-89.
International Searching Authority, International Search Report and Written Opinion for application PCT/US2017/015434, dated Apr. 5, 2017.
Jurysta C, et al. Salivary glucose concentration and excretion in normal and diabetic subjects. BioMed Res Int 2009;2009.
Karjalainen K, et al. Salivary factors in children and adolescents with insulin-dependent diabetes mellitus. Pediatr Dent 1995;18:306-11.
Katz LB, et al. A comprehensive evaluation of strip performance in multiple blood glucose monitoring systems. Expert Rev Med Devices 2015;12:263-71.
Klasner SA, et al. Paper-based microfluidic devices for analysis of clinically relevant analytes present in urine and saliva. Anal Bioanal Chem 2010;397:1821-9.
Kumar S, et al. Correlation of salivary glucose, blood glucose and oral candidal carriage in the saliva of type 2 diabetics: A case-control study. Contemp Clin Dent 2014;5:312. doi:10.4103/0976-237X.137925.
La Belle JT, et al. A disposable tear glucose biosensor—part 2: system integration and model validation. J Diabetes Sci Technol 2010;4:307-11.
La Belle JT, et al. A Disposable Tear Glucose Biosensor—Part 4 Preliminary Animal Model Study Assessing Efficacy, Safety, and Feasibility. J Diabetes Sci Technol 2014;8:109-16.
Lan K, et al. A disposable tear glucose biosensor—part 3: assessment of enzymatic specificity. J Diabetes Sci Technol 2011;5:1108-15.
Langer O, et al. Glycemic control in gestational diabetes mellitus—how tight is tight enough: small for gestational age versus large for gestational age? Am J Obstet Gynecol 1989;161:646-53.
Liao Y-T, et al. A 3-CMOS glucose sensor for wireless contact-lens tear glucose monitoring. Solid-State Circuits IEEE J of 2012;47:335-44.
Manaviat MR, et al. Prevalence of dry eye syndrome and diabetic retinopathy in type 2 diabetic patients. BMC Ophthalmol 2008;8:10.
Mandel ID. Sialochemistry in diseases and clinical situations affecting salivary glands. CRC Crit Rev Clin Lab Sci 1980;12:321-66.
Marchetti P, et al. Decreased salivary glucose secretory rate: usefulness for detection of diabetic patients with autonomic neuropathy. Diabetes Res Clin Pract 1989;7:181-6.
Olokoba AB, et al. Type 2 Diabetes Mellitus: A Review of Current Trends. Oman Med J 2012;27:269-73.
Ong WM, et al. Barriers and facilitators to self-monitoring of blood glucose in people with type 2 diabetes using insulin: a qualitative study. Patient Prefer Adherence 2014;8:237-46.
Panchbhai AS. Correlation of Salivary Glucose Level with Blood Glucose Level in Diabetes Mellitus. J Oral Maxillofac Res 2012;3.
Ravindran R, et al. Estimation of Salivary Glucose and Glycogen Content in Exfoliated Buccal Mucosal Cells of Patients with Type II Diabetes Mellitus. J Clin Diagn Res JCDR 2015;9:ZC89.
Reuterving C, et al. Salivary flow rate and salivary glucose concentration in patients with diabetes mellitus influence of severity of diabetes. Diabete Metab 1986;13:457-62.
Soni A, et al. A paper strip based non-invasive glucose biosensor for salivary analysis. Biosens Bioelectron 2015;67:763-8.
Stettler C, et al. Glycemic control and macrovascular disease in types 1 and 2 diabetes mellitus: meta-analysis of randomized trials. Am Heart J 2006;152:27-38.

(56) References Cited

OTHER PUBLICATIONS

Vaddiraju S, et al. Technologies for continuous glucose monitoring: current problems and future promises. J Diabetes Sci Technol 2010;4:1540-62.
Yamaguchi M, et al. Noninvasively measuring blood glucose using saliva. Eng Med Biol Mag IEEE 1998;17:59-63.
Zhang W, et al. Noninvasive glucose monitoring using saliva nano-biosensor. Sens Bio-Sens Res 2015;4:23-9.
U.S. Appl. No. 16/482,661.
U.S. Appl. No. 16/495,682.
U.S. Appl. No. 16/543,400.

\* cited by examiner

A little background...

Tear Glucose

User touches device to conjunctiva, collecting tear fluid.

In 9 seconds, glucose levels are displayed.

The relationship between blood glucose and tear glucose has been successfully identified.

PHOTOGRAPH: device use. INSET: sensor depicting integrated (A) absorbent capture material, (B) microfluidic channel, (C) sensor-assay area and (D), sensor strip.

LAG TIME BETWEEN SALIVA GLUCOSE AND BLOOD GLUCOSE (LESS THAN 20 SECONDS)

FIG. 4A

CLARKE ERROR GRID RELATING BLOOD GLUCOSE VALUES AS MEASURE USING SMBG AND THE SALIVA GLUCOSE TECHNOLOGY.

SALIVA GLUCOSE MEASUREMENT DEVICES AND METHODS

CROSS-REFERENCE TO RELATED APPLICATIONS

This application represents the U.S. National Stage entry of PCT/US2017/015434, filed on Jan. 27, 2017, and claims priority to U.S. Provisional Patent Application No. 62/288,747 filed on Jan. 29, 2016.

FIELD OF THE INVENTION

This disclosure relates to devices and methods of measuring glucose in saliva.

BACKGROUND OF THE INVENTION

Blood glucose levels commonly are assessed using a blood sample. It is desirable to utilize less- or non-invasively obtained fluid samples for assessing blood glucose levels.

SUMMARY OF THE INVENTION

Devices and methods are disclosed that are capable of detecting glucose in saliva as a surrogate for blood glucose levels. The devices feature a sensor having a substrate containing electrodes and one or more reagents on the electrodes. A detection device is operably coupled with the sensor to detect glucose based on measurement of an electrical parameter when electricity is applied to the electrodes.

In the disclosure that follows, the diagnostic relationship between blood glucose and saliva glucose was determined in order to create a non-invasive technology, which can be utilized, for example, by diabetics to control their disease.

BRIEF DESCRIPTION OF THE DRAWINGS

FIG. 7. Clark Error Grid: The Clark Error grid helped to map the data points in reference to an FDA approved reference device (One Touch Ultra SMBG). From this study, 22.1% of results fell in region A, which is the ideal region indicating an error margin under 20%. 76.6% of results fell in region B, which indicates readings with greater than 20% error but still accurate enough to prevent patient harm. The remaining 1.3% of results fell in category C, which indicated a measurement with a chance of causing unnecessary treat-ment. No results fell into categories D or E, which would indicate a potentially dangerous failure to detect hypogly-cemia or hyperglycemia.

FIG. 8. This schematic representation is of a glucose detection mechanism. A) Collection of saliva by naturally salivating. B) Pipette transfer of the sample onto the SG sensor at which (B1) the glucose is catalyzed by GDH-FAD enzyme the resulting electrons are detected by the sensor under an electron mediator, potassium ferricyanide. C) Data processing, where (C1) the electrical current generated after a set amount of time is recorded into the system and be matched against a (C2) calibration curve, which then cal-culates the glucose concentration and display the result on D) a monitor.

FIG. 9. The left portion of FIG. 9 is a CV of the GDH modified sensor in saliva with 50 mg/dL of glucose. The red circle indicates current value observed in Amp-it when 0.35V is applied. The right side shows the calibration curve of the linear relationship between glucose concentrations in saliva (mg/dL) and the current (A). The glucose concentra-tions tested were 0, 0.5, 1, 2, 4, 10, 20, 100, and 200 mg/dL, each with 3 replications and error bars shown. The linear relationship is characterized as Y=−1.05E-07X-4.93E-07 with R2 value of 0.99, where Y is the electrical current in A and X is the glucose concentration in mg/dL.

FIG. 10.

FIG. 11. FIG. 11 shows the correlation of SG-BG among all subjects. Data points from faulty sensors and mishan-dling were removed. The slope is characterized by Y=0.6808X-16.608 with an R-square value of 0.78.

DETAILED DESCRIPTION OF THE INVENTION

Figure 12:
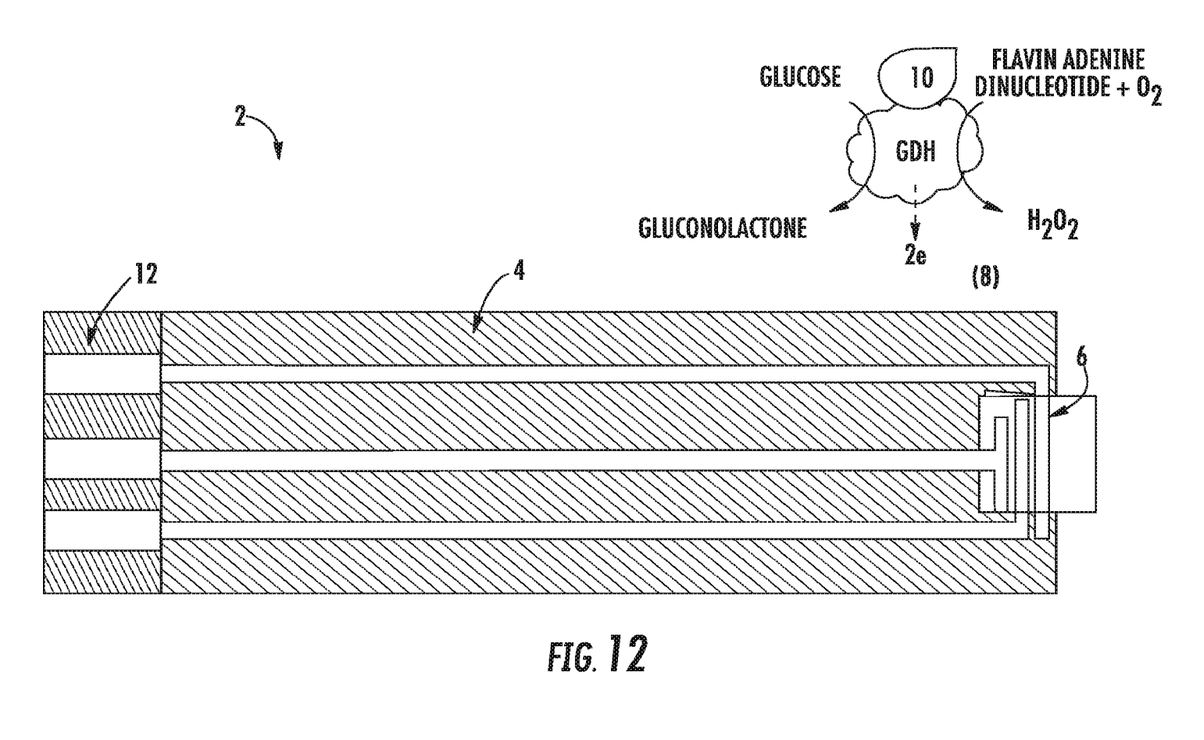
FIG. 12. This figure schematically depicts a sensor embodiment and system for detection of glucose in saliva.

Embodiments of a device capable of detecting glucose in saliva are disclosed. In one example as shown in FIG. 12, the sensor device 2 includes a substrate 4 containing electrodes 6 and one or more reagents on the electrodes (collectively shown by arrow 8). For example, the reagents may include glucose dehydrogenase (GDH) and an electron mediator, such as ferricyanide or Flavin adenine dinucleotide in 1×PBS buffer. Preferably, the one or more reagents are in dry form and applied to the electrodes prior to contact with a saliva sample 10.

A detection device 12 is operably coupled with the sensor to detect glucose based on measurement of an electrical parameter when electricity is applied to the electrodes on the sensor where the saliva sample resides. For example, the detection device 12 collectively may include a power supply, data processor and programing to record the electrical current generated after a set amount of time into the system and match it against a calibration curve, which then calculates the glucose concentration and displays the result on a monitor. In one embodiment such a system is a commercially available electrochemical analyzer (Model 1230A analyzer from CH Instruments, Inc.) and amperometric-current-over-time (Amp i-t) assay. Of course, a tablet or smart phone may additionally or alternatively be used with or as the monitor of the detection system with appropriate wired or wireless components and settings.

The sensor device may further include a Nafion (i.e., a sulfonated tetrafluoroethylene based fluoropolymer-copolymer) coating or mesoporous carbon coating on the electrodes to reduce nonspecific binding and/or amplify the signal.

From the above embodiment, it can readily be appreciated that a method of detecting a blood glucose level using saliva also is disclosed. The method in this embodiment includes contacting a sensor containing electrodes and one or more reagents on the electrodes with saliva on the electrodes. Next, electricity is applied to the electrodes such that a measurement of an electrical parameter indicative of an amount of glucose is produced when electricity is applied.

EXAMPLES

A test was conducted of 20 individuals (10 diabetic, 5 Type 1 Diabetes, 5 Type 2 Diabetes) as follows:

Collected SMGB data and tested saliva using the SG device.

Determine correlation between saliva glucose and blood glucose levels.

Evaluate feasibility of saliva capture method.

Determine typical lag time between SG and BG elevation.

Allow saliva to build up in the mouth for approximately thirty seconds.

Deposit saliva on to a curved metal applicator.

Once devices and software are ready, tilt the applicator so that saliva falls onto the electrode of the device.

All devices contain dry reagent applied onto the electrodes earlier.

Reagents: 1.5 mg of GDH: 1 mL of ferricyanide in 1×PBS buffer solution.

Run amperometric-i-t curve for 30 seconds with an initial voltage of 0.35V and a sensitivity of 1E-5.

Take blood glucose measurement using SMBG.

Take 15 g glucose solution orally.

Rinse 3× for 3 seconds each.

Wait 10 minutes.

Repeat steps 1-5.

Then repeat steps 1-5 every 15 minutes up until 60 minutes. After 60 minutes, repeat steps 1-5 every 30 minutes until 180 minutes total have elapsed. Stop the experiment with a total of 10 data points.

Due to manufacturing inconsistencies, a total of 19 devices had to be discarded for failure to read accurately. There are several factors that cause errors, noises and outliers which affect final results.

Drinking water:
    Drinking water during the experiment might affect the final result because it could dilute the concentration of glucose in saliva especially when the time between every test is only 15 minutes.

Bubbles:
    When a subject bubbly saliva, not clear, the i-t curves contains number of noises and spikes. (See FIGS. 1, 2, 3 and 4)

Dry vs wet reagent:
    Since swirling the Saliva and the dry reagent together before running the software was not a step in the procedure, the reagent might not be well-mixed with the glucose concentration, Saliva. Therefore not accurate result.

Using the saliva glucose prototype sensor: Significant correlation between BG and SG has been achieved. The saliva glucose sensor has the potential to predict BG. Average lag time is approximately 15 minutes. In accordance with ISO 15197-2013, 98.7% likely to provide a reading which would not harm a patient.

Figure 1:
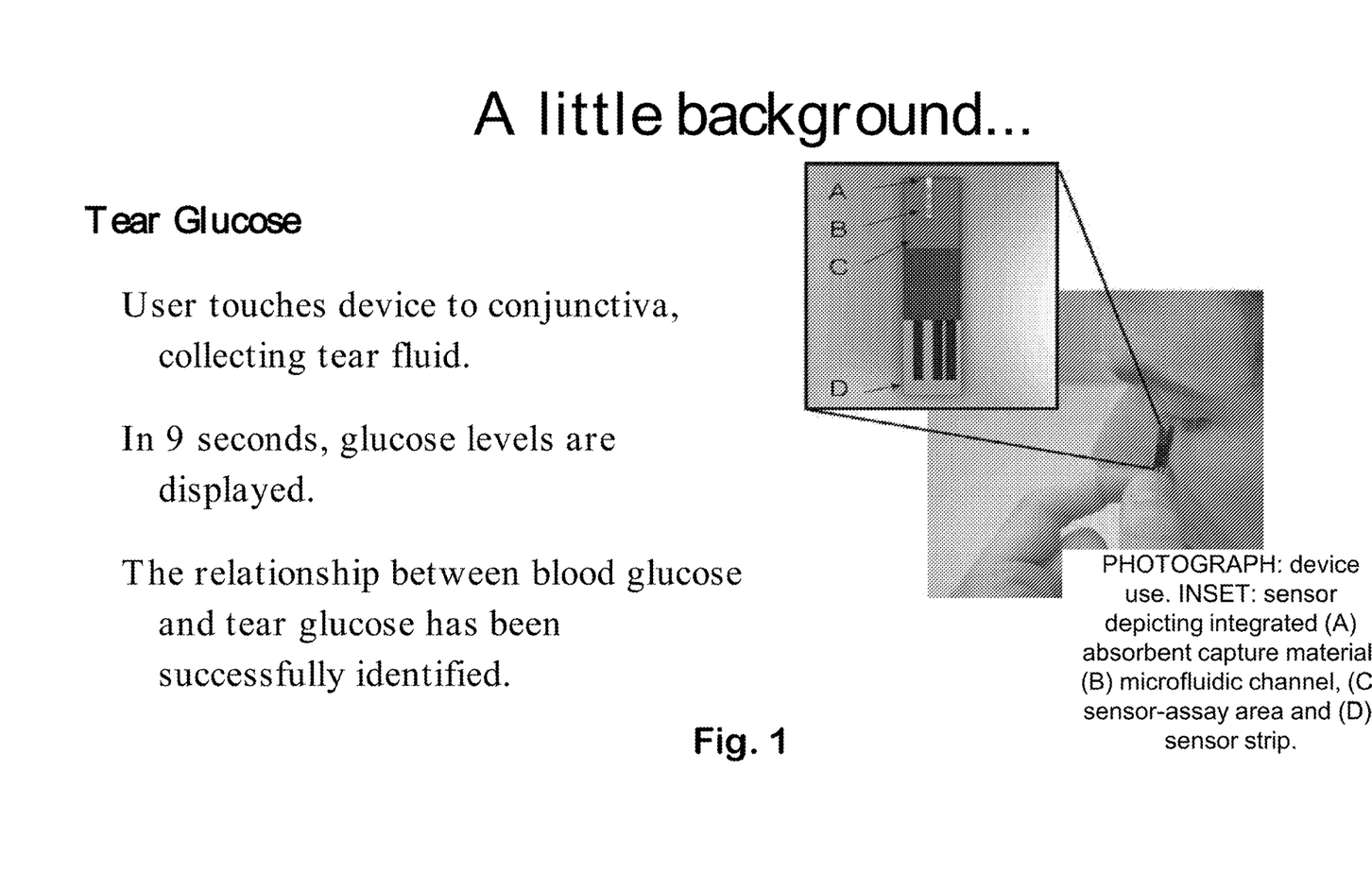
FIG. 1 depicts a glucose sensor for tear fluid.
Figure 2:
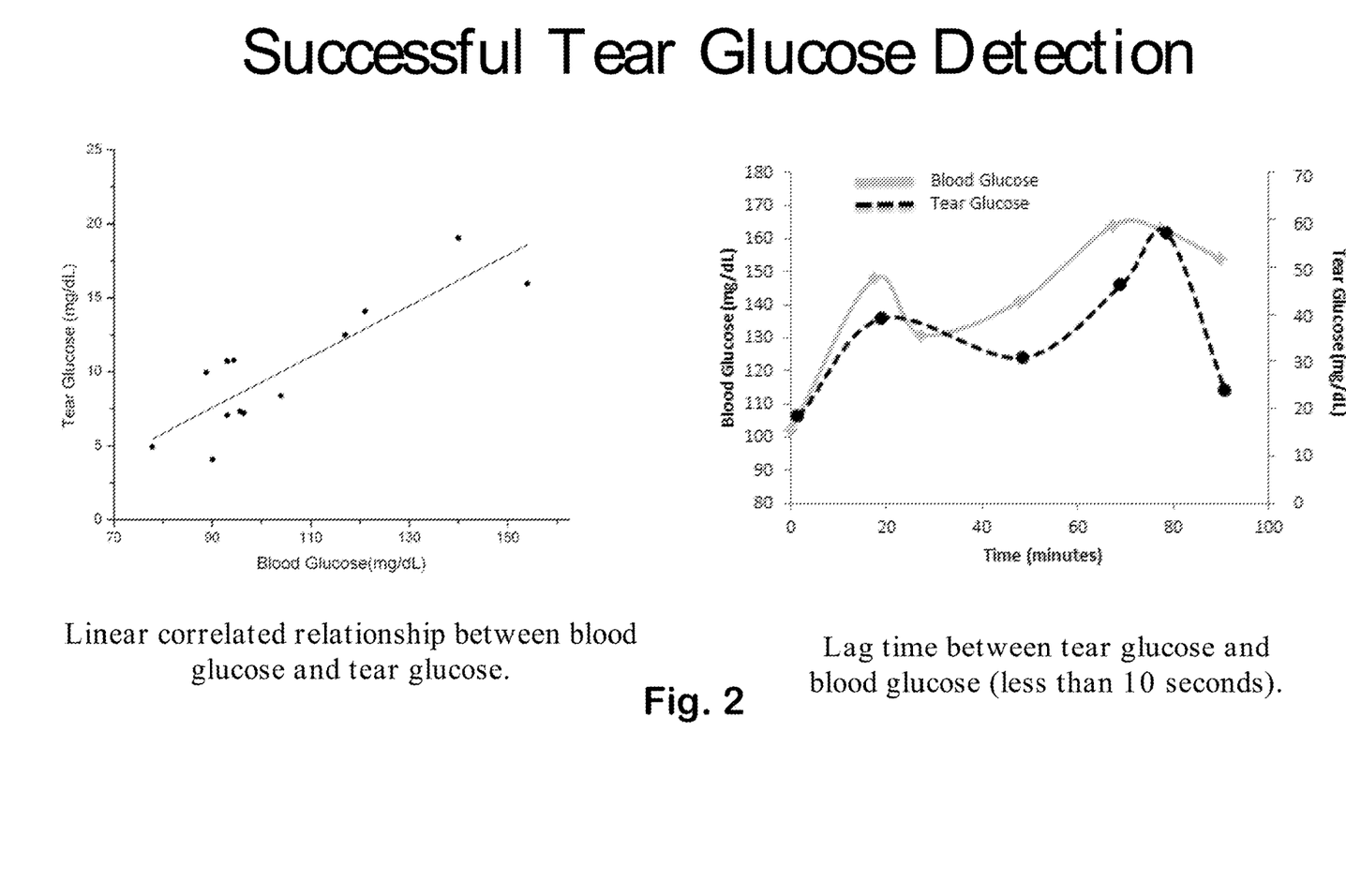
FIG. 2 depicts data for tear fluid measurement of glucose.
Figure 3:
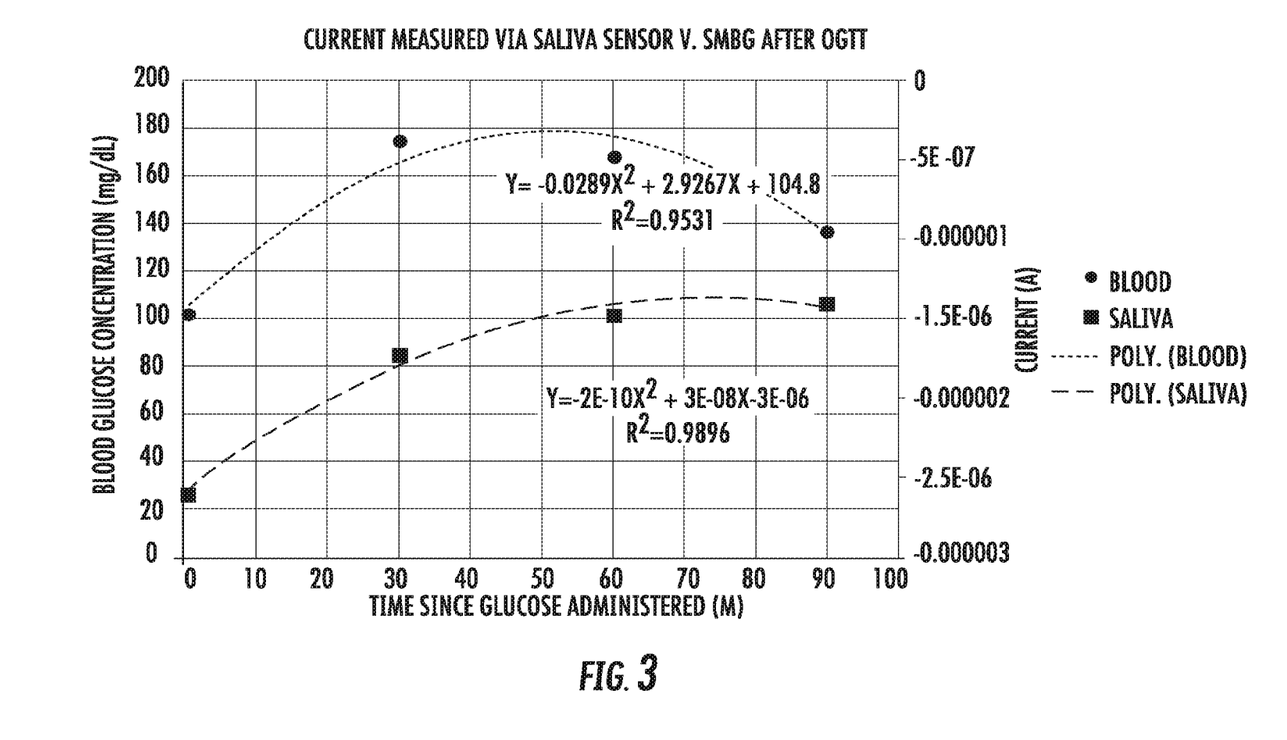
FIG. 3 depicts comparative data for blood versus tear glucose detection.
Figure 4A:
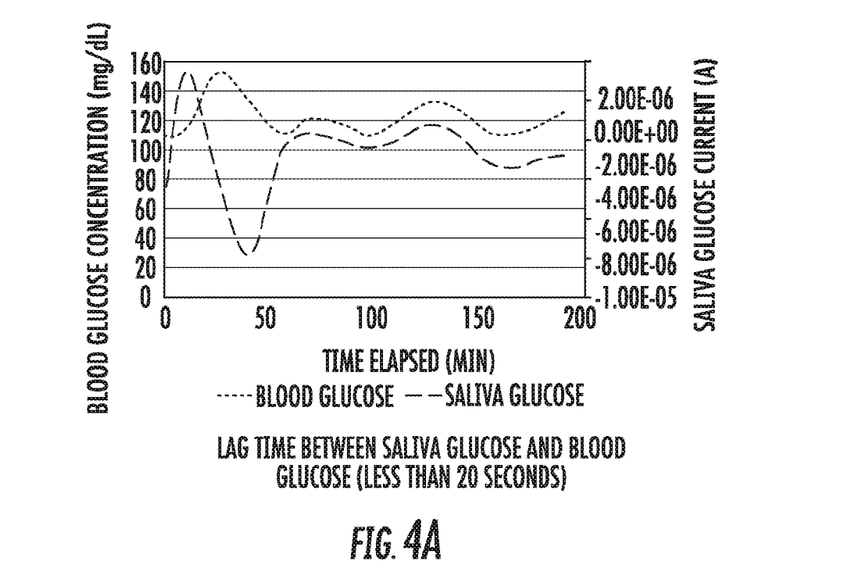
FIG. 4A shows multiple measurements taken on a subject before OGTT and after while monitoring blood and saliva glucose simultaneously.
Figure 4B:
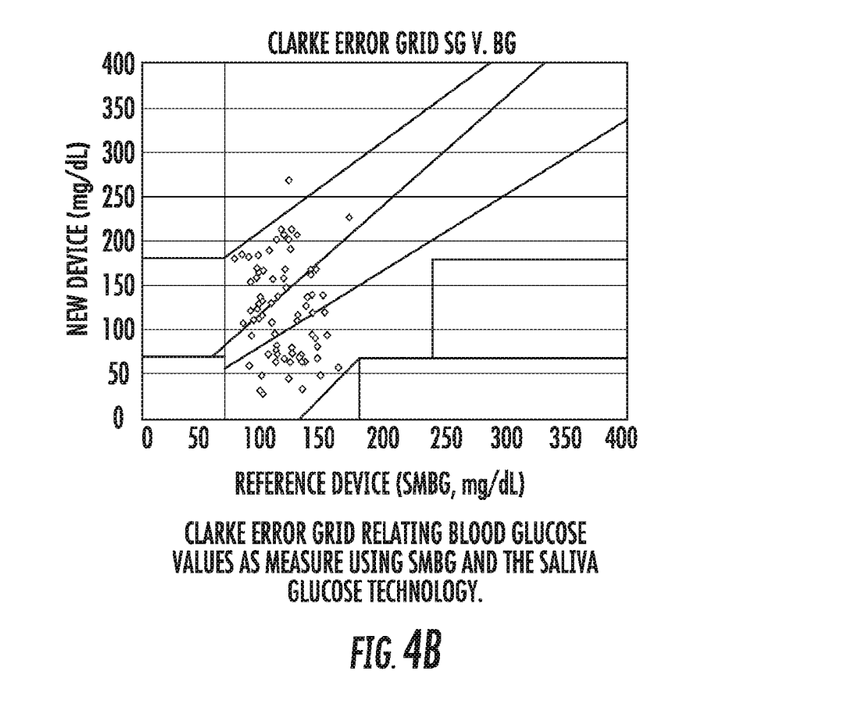
FIG. 4B depicts a Clarke Error grid of the resulting study (from the data in 4A) showing a correlation between saliva and self-monitored blood glucose in a number of subjects. Most data is found in region A and B (safe regions).
Figure 5:
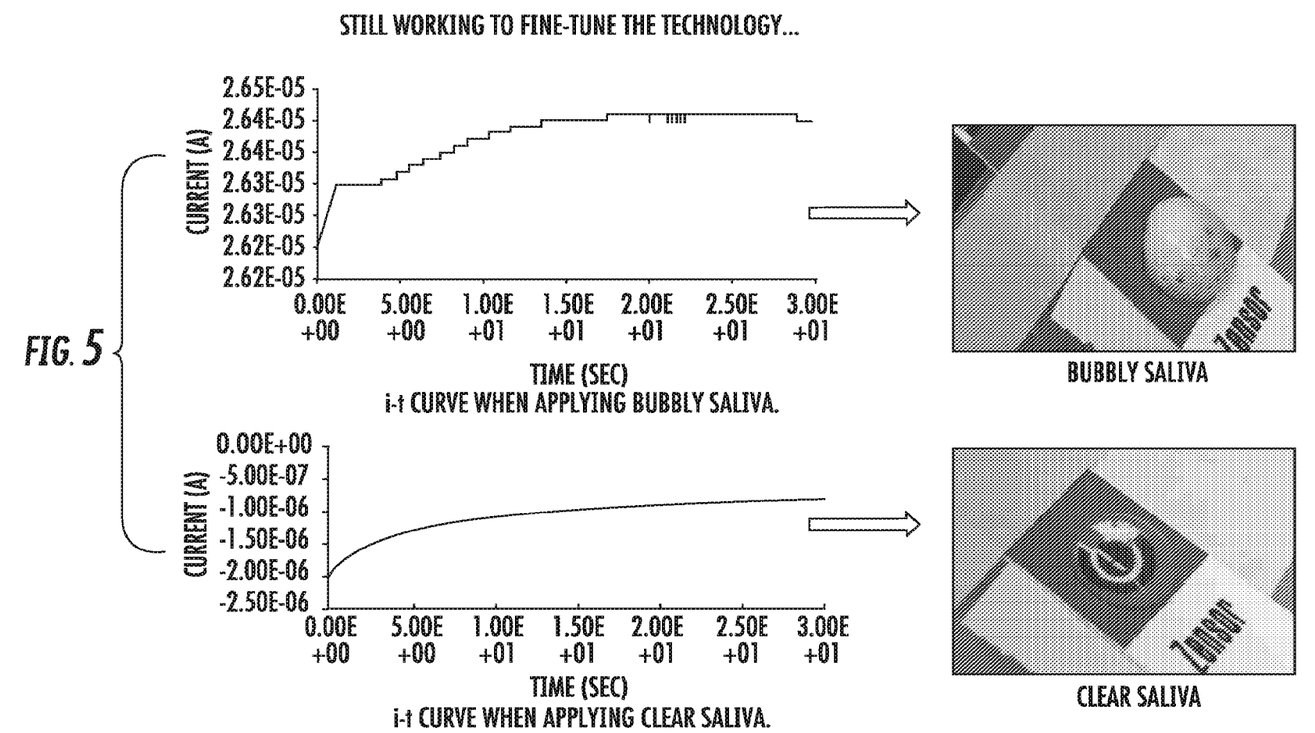
FIG. 5 shows the average lag time between the peaks of SMBG level and saliva glucose current. There are two outliers, subjects E and F. Although subject F has a relatively short lag time, the device failure for subject F makes the time inaccurate. Some device failed while gathering subject E and F's data which skewed the lag time. Subject E and F are thus considered outliers are excluded from the analysis. After avoiding those errors, we notice that the following subjects, H, I and J, have close values of lag time. The average lag time of all 10 subject is 24 minutes. The average lag time without outliers, E and F, is 15 minutes.
Figure 6:
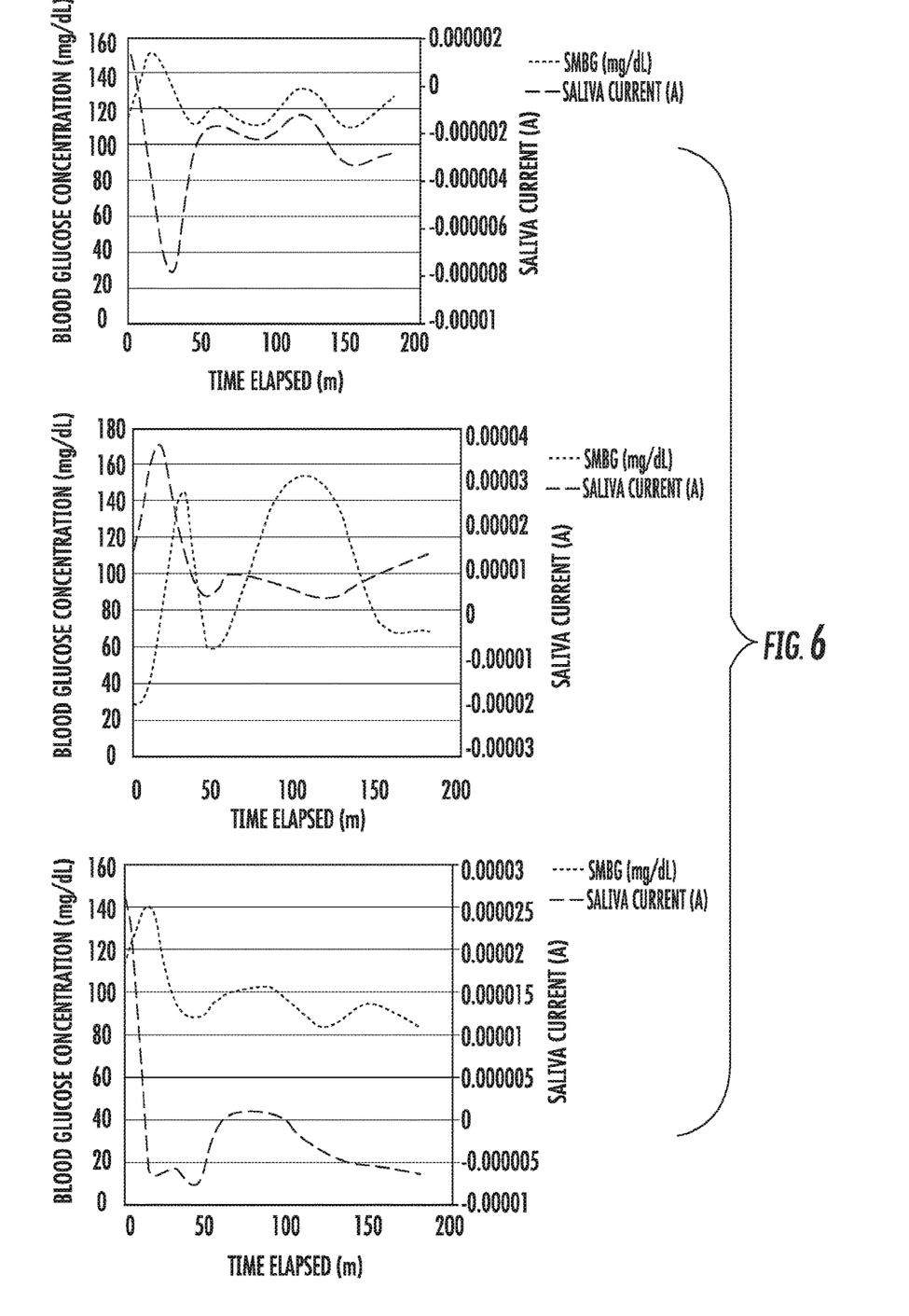
FIG. 6. The graphs at FIG. 6 show the change in blood-glucose and saliva-glucose over time after three hours of oral glucose challenge test. The graphs suggest that saliva glucose correlates with blood glucose over time. Possible sources of variance include: individual variation in mouth rinsing, Bubbles and viscosity of saliva samples, and manu-facturing variance (hand-made devices).
Figure 7:
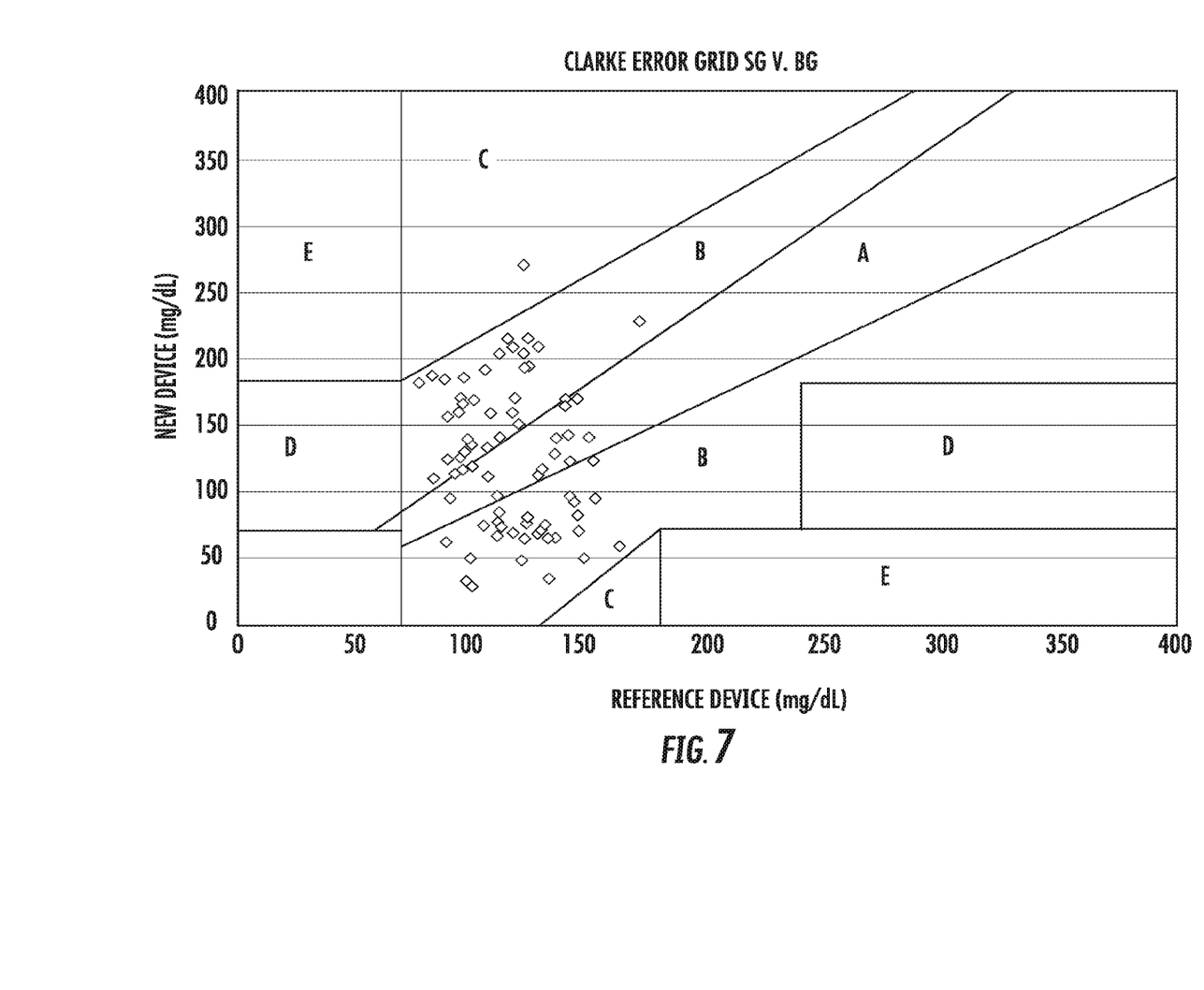
Figure 8:
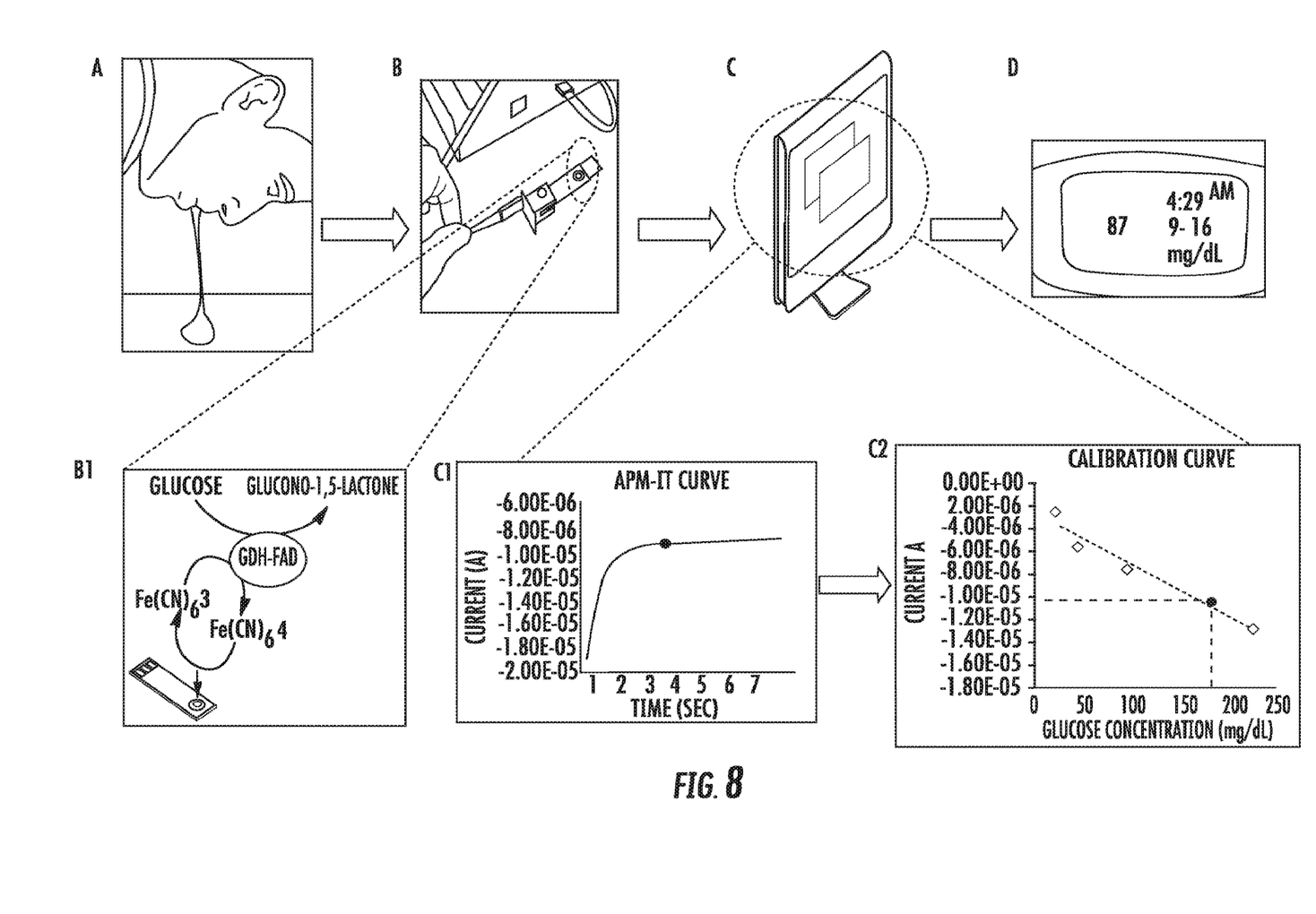

This disclosure aims to illustrate the design and development of the first disposable SG sensor employing glucose dehydrogenase flavine-adenine dinucleotide (GDH-FAD) capable of quantify SG levels without any sample preparation. The electrochemical approach is outlined in FIG. 8. The sensor employed in this work is a commercially available screen printed sensor, Zensor, which can be acquired from CH-Instrument, Texas. It is composed of a carbon working electrode, a carbon counter electrode, and an Ag/AgCl reference electrode.

The detection reagent is prepared by mixing 1 mL of 100 mM potassium ferricyanide with 1.5 mg of GDH-FAD enzyme. 100 mM potassium ferricyanide is prepared in pH 7.4 1× Phosphate Buffer Saline (PBS). GDH-FAD is highly specific to glucose and is not reactive to other sugars with the exception of xylose. GDH-FAD also employs a signal-to-noise ratio that is 9 times higher than that of glucose oxidase. It has been reported that GDH-FAD has 25 times more enzymatic activity than glucose oxidase, which permits rapid glucose sensing. Dried sensors are prepared by pipetting 27 uL of the reagent onto the sensing well with uniform coverage of all 3 electrodes. The sensors are then placed in a dehydrator at 30° C. for 25 minutes to dry the reagent completely. The completed sensors are carefully examined for visible defects. Sensors with dried reagents outside the sensing well or incomplete coverage of all 3 electrodes were not used for testing. Completed sensors can be stored at room temperature for up to 12 weeks.

Figure 9A:
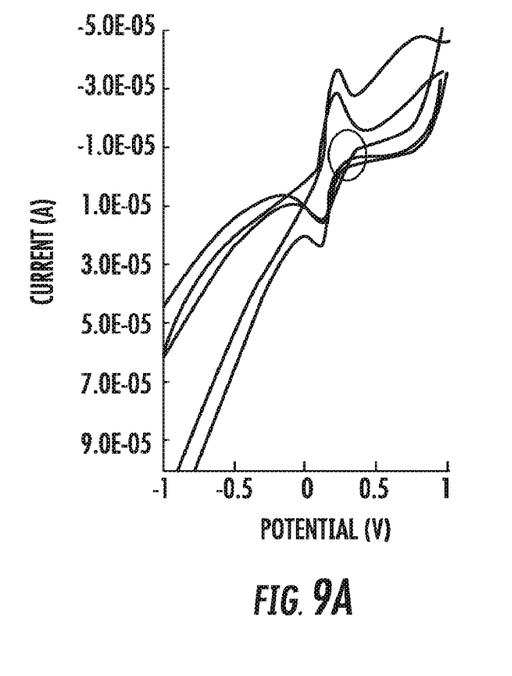
Figure 9B:
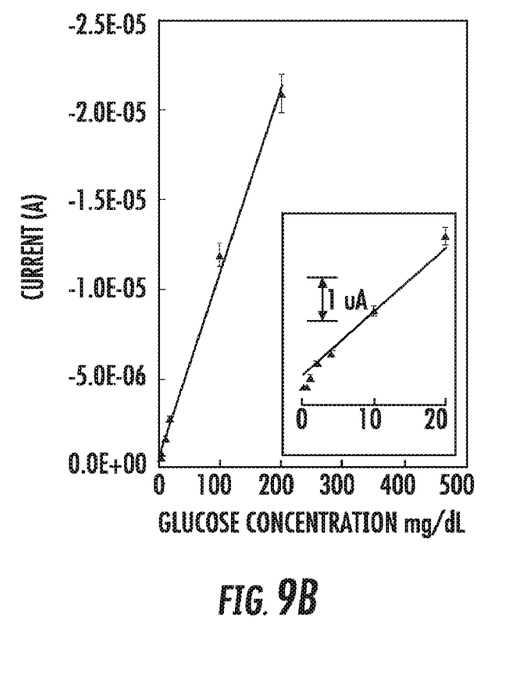

Completed sensors are then tested against various concentrations of glucose (120 µL sample volume) in saliva using an electrochemical analyzer (1230A CH-instrument) and amperometric-current-over-time (Amp i-t) assay for 30 seconds. Cyclic voltammetry (CV) was first conducted in saliva to determine the potential for Amp i-t assay (FIG. 9). After evaluating the signal strength and noise of various potentials using Amp-it, a bias potential of 0.35 V was deemed appropriate as it has the lowest noise. This potential was chosen to test all sensors at varying glucose concentrations. A correlation analysis was then conducted to evaluate current readings at several time stamps (t=10, 20, 30 s.) It was determined that the electrical current signal at t=10 is a good representative signal for the sample. A calibration curve, at the 10 second mark, has been constructed and is shown in FIG. 9. According to the calibration curve, the dynamic range of the sensor is projected to encompass glucose concentrations spanning from 1.23 mg/dL to 247.07 mg/dL, which covers the clinically relevant SG range of DM subjects reported in literature.

A preliminary clinical study of 9 non-DM subjects and 3 type 1 DM subjects age 19-25 years (mean age of 23+/−1) was conducted. The study was approved by the Arizona State University Institutional Review Board (IRB) under the identification number of STUDY00002778. All procedures and tests were in compliance with IRB requirements. The sample collection steps are as follows.

Each subject was asked to rinse their mouth with fresh water 3 times for 3 seconds each time. The subject was then asked to accumulate saliva for 30 seconds, and deposit it onto a sterilized metal lab spatula. Ten seconds later, a 120 µL sample of saliva was then transferred, via a pipet tip, to the saliva glucose sensor pre-connected to the electrochemical analyzer. The saliva sample did not undergo any sample preparation or purification prior to testing. Immediately following the deposition of saliva, amperometric i-t technique was performed at a voltage of 0.35 V. The current readings at t=10 seconds are used as the representative signal for the SG measurement, and have been utilized to determine the appropriate SG concentration. The entire SG measuring process from sampling to obtaining the corresponding current measurement is approximately 1 minute, which is much faster than those ranging from 10 to 20 minutes. Given the short duration of testing, the potential breakdown of glucose by bacteria can be avoided.

Figure 10:
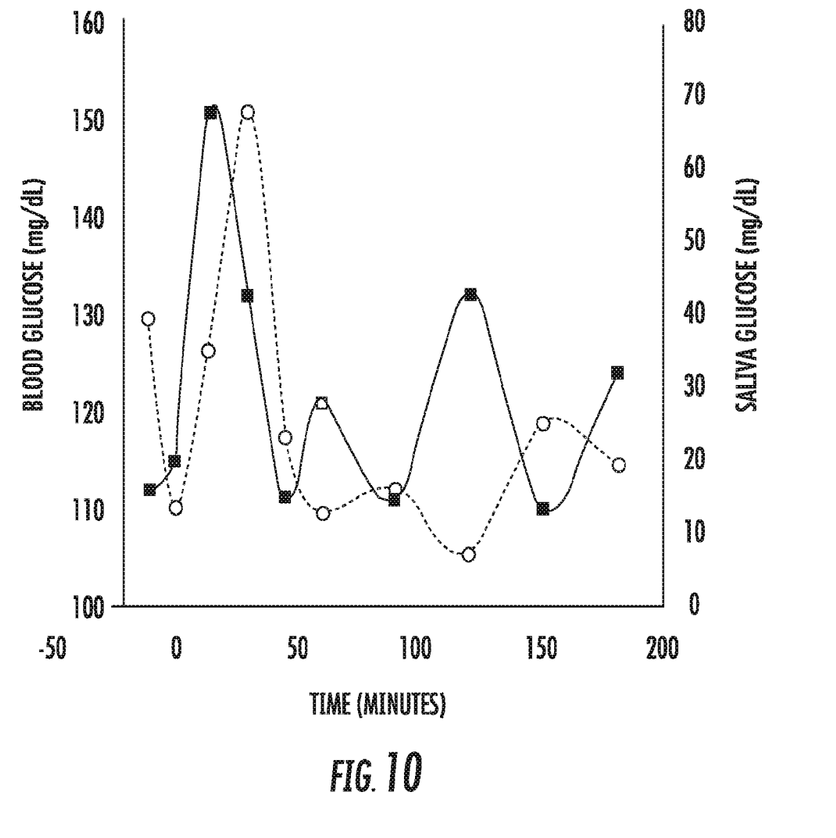
FIG. 10 shows how the saliva glucose tracks blood glucose in a non-diabetic subject using disposable SG sensors. The solid squares and lines represent blood glucose measurements and trends. The hollow circles and dashed lines represent saliva glucose measurements and trends. The time stamps are −10, 0, 15, 30, 45, 60, 90, 120, 150, and 180 minutes. The oral glucose challenge was given at t=0 minutes.

To avoid potential stress induced on diabetic subjects, glucose tolerance testing was performed only on the 9 non-diabetic subjects by administering a 15 gram glucose shot orally (at t=0 min). After the subject swallowed the glucose shot, he/she was then instructed to immediately rinse their mouth with fresh water 3 times for 3 seconds each time. The SG and BG were then measured every 15 minutes until t=60 minutes, then were measured once every 30 minutes until t=180 minutes using the same procedure described above. One representing subject's SG-BG tracking data is shown in FIG. 10.

Figure 11:
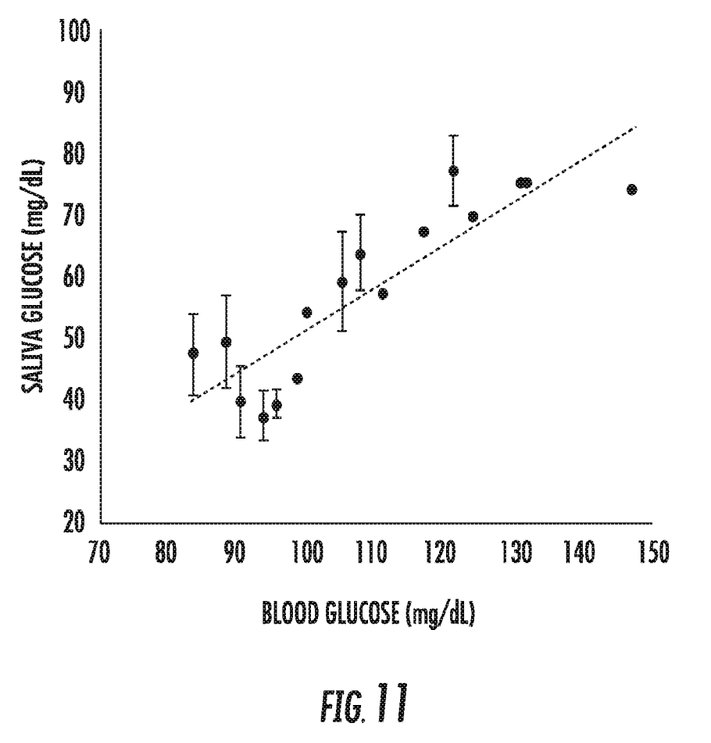

All SG values from healthy and DM subjects, excluding data points generated by compromised sensors and linked to traceable human error, are plotted against the SMBG values, shown in FIG. 11. The average measured SG range for all subject ranges from 34.4 mg/dL to 76.6 mg/dL corresponding to a BG range from 83 mg/dL to 147 mg/dL which contradicts the SG values ranging from 0.19-3.82 mg/dL and the SG values ranging from 4-13 mg/dL. This disconnect may be attributed to how rapidly the saliva glucose is measured after sample collection and the prevalence of glycolysis.

Given the sensor can measure glucose in approximately 25 seconds (15 seconds for sample collection and a 10 second duration before the utilized current readings are collected), it is possible to obtain higher saliva glucose measurements when compared to the 5-20 minute processing times of other techniques. Nevertheless, The SG seems to track BG well with a lag time ranging from −15 minutes to 15 minutes, which is consistent with literature. The lag time can be attributed to individual dietary patterns, lifestyles, and race. A positive correlation between SG and BG is also identified, which is consistent with literature.

In summary, an easy-to-use, rapid, and disposable SG sensor featuring GDH-FAD and no sample preparation is underway.

The following claims are not intended to be limited by the embodiments and examples herein.

What is claimed is:

1. A method of detecting a blood glucose level using saliva, the method comprising:
   contacting a sensor containing electrodes and one or more glucose-detection reagents on said electrodes with saliva; and
   energizing said electrodes such that a measurement of an electrical parameter indicative of an amount of glucose in said saliva is produced and measured,
   wherein said one or more glucose-detection reagents comprise glucose dehydrogenase (GDH) and ferricyanide in 1X phosphate buffered saline (PBS) buffer.

2. A method of detecting a blood glucose level using saliva, the method comprising:
   contacting a sensor containing electrodes and one or more glucose-detection reagents on said electrodes with saliva; and
   energizing said electrodes such that a measurement of an electrical parameter indicative of an amount of glucose in said saliva is produced and measured, wherein said one or more reagents comprise glucose dehydrogenase flavine-adenine dinucleotide (GDH-FAD) and ferricyanide in 1×PBS buffer.

3. A method of monitoring a glucose level against a desired range in a patient, comprising:
   contacting a sensor containing electrodes and one or more glucose-detection reagents on said electrodes with saliva; and
   energizing said electrodes such that a measurement of an electrical parameter indicative of an amount of glucose in said saliva is produced and measured against said desired range,
   wherein said one or more glucose-detection reagents comprise glucose dehydrogenase (GDH) and ferricyanide in 1×PBS buffer.

4. The method of claim 3, further including a sulfonated tetrafluoroethylene-based fluoropolymer-copolymer coating or mesoporous carbon coating on one or more of the electrodes.

5. The method of claim 3, wherein said glucose-detection reagents are dried prior to contacting with the saliva.

6. A method of monitoring a glucose level against a desired range in a patient, comprising:
   contacting a sensor containing electrodes and one or more glucose-detection reagents on said electrodes with saliva; and
   energizing said electrodes such that a measurement of an electrical parameter indicative of an amount of glucose in said saliva is produced and measured against said desired range, wherein said one or more reagents comprise glucose dehydrogenase flavine-adenine dinucleotide (GDH-FAD) and ferricyanide in 1×PBS buffer.

* * * * *

UNITED STATES PATENT AND TRADEMARK OFFICE
CERTIFICATE OF CORRECTION

PATENT NO. : 10,724,066 B2
APPLICATION NO. : 16/068877
DATED : July 28, 2020
INVENTOR(S) : Jeffrey LaBelle et al.

Page 1 of 1

It is certified that error appears in the above-identified patent and that said Letters Patent is hereby corrected as shown below:

In the Specification

Column 2, Line 60, "1×PBS" should be --1X PBS--.

Column 3, Line 45, "1×PBS" should be --1X PBS--.

Column 4, Line 29, "1× Phosphate" should be --1X Phosphate--.

In the Claims

Column 6, Claim 2, Line 25, "1×PBS" should be --1X PBS--.

Column 6, Claim 3, Line 38, "1×PBS" should be --1X PBS--.

Column 6, Claim 6, Line 54, "1×PBS" should be --1X PBS--.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*